United States Patent
Wiley et al.

(10) Patent No.: US 12,014,506 B1
(45) Date of Patent: Jun. 18, 2024

(54) METHOD AND SYSTEM FOR ALIGNING REFERENCE LANDMARKS TO FEATURES WITHIN A THREE-DIMENSIONAL SPACE

(71) Applicant: Stratovan Corporation, Davis, CA (US)

(72) Inventors: David F. Wiley, Davis, CA (US); Wesley Castro, Davis, CA (US)

(73) Assignee: Stratovan Corporation, Davis, CA (US)

(*) Notice: Subject to any disclaimer, the term of this patent is extended or adjusted under 35 U.S.C. 154(b) by 433 days.

(21) Appl. No.: 17/496,701

(22) Filed: Oct. 7, 2021

(51) Int. Cl.
*G06T 7/33* (2017.01)
*A61C 9/00* (2006.01)
*G06T 3/18* (2024.01)
*G06T 7/73* (2017.01)
*G16H 50/50* (2018.01)

(52) U.S. Cl.
CPC ............ *G06T 7/344* (2017.01); *A61C 9/0053* (2013.01); *G06T 3/18* (2024.01); *G06T 7/75* (2017.01); *G16H 50/50* (2018.01)

(58) Field of Classification Search
CPC .. G06T 7/344; G06T 7/75; G06T 3/18; G16H 50/50; A61C 9/0053
USPC ......................................................... 382/103
See application file for complete search history.

(56) References Cited

U.S. PATENT DOCUMENTS

| | | | |
|---|---|---|---|
| 2009/0187388 A1* | 7/2009 | Shu ........................ | G06V 10/84 703/2 |
| 2018/0365512 A1* | 12/2018 | Molchanov ............ | G06V 10/82 |
| 2021/0186355 A1* | 6/2021 | Ben-Yishai ............ | A61B 34/10 |
| 2022/0058822 A1* | 2/2022 | Naruniec ................ | G06N 5/04 |

FOREIGN PATENT DOCUMENTS

WO   WO-2021074871 A1 *   4/2021   ............... G06T 7/73

* cited by examiner

*Primary Examiner* — Gabriel I Garcia
(74) *Attorney, Agent, or Firm* — Foley & Lardner LLP

(57) ABSTRACT

Example implementations include a method of locating landmarks at a target object model by obtaining a target model associated with a target physical object, and a reference model associated with a reference physical object and including an anchor landmark coordinate, generating a convergence metric based on a structural property of the target model at the anchor landmark coordinate, a structural property of the reference model at the landmark coordinate, and an alignment resolution associated with a first quantized distance, and in accordance with a determination that the convergence metric satisfies a convergence heuristic and does not satisfy a resolution heuristic, associating the alignment resolution with a second quantized distance less than the first quantized distance, and modifying a position of the anchor landmark coordinate based on the alignment resolution.

20 Claims, 12 Drawing Sheets

METHOD AND SYSTEM FOR ALIGNING REFERENCE LANDMARKS TO FEATURES WITHIN A THREE-DIMENSIONAL SPACE

TECHNICAL FIELD

The present implementations relate generally to three-dimensional (3D) imaging, and more particularly to aligning reference landmarks to features within a three-dimensional space.

BACKGROUND

Biomedical imaging requires increasing complex biomedical data input and computational processing to achieve successful medical outcomes. Conventional systems may not effectively process biomedical imaging information with sufficient speed and at sufficient granularity to support individualized patient care.

SUMMARY

It is advantageous to simplify the generation of models that represent physical structures and to reduce computational expense of generating models adaptable to a broad range of permutations in physical structures. It is further advantageous to generate a target model including landmarks located proximate to various physical features as representations of those physical features. Example implementations can include an iterative process of placing landmarks at a target model based on an iterative process and can further include a second optionally iterative process for placing further landmarks at the target model. Thus, a technological solution for aligning reference landmarks to features within a three-dimensional space is provided.

Example implementations include a method of locating landmarks at a target object model by obtaining a target model associated with a target physical object, and a reference model associated with a reference physical object and including an anchor landmark coordinate, generating a convergence metric based on a structural property of the target model at the anchor landmark coordinate, a structural property of the reference model at the landmark coordinate, and an alignment resolution associated with a first quantized distance, and in accordance with a determination that the convergence metric satisfies a convergence heuristic and does not satisfy a resolution heuristic, associating the alignment resolution with a second quantized distance less than the first quantized distance, and modifying a position of the anchor landmark coordinate based on the alignment resolution.

Example implementations also include a system of locating landmarks at a target object model, with a coarse alignment engine operable to obtain a target model associated with a target physical object, and a reference model associated with a reference physical object and including an anchor landmark coordinate, a refinement engine operatively coupled to the coarse alignment engine and operable to generate a convergence metric based on a structural property of the target model at the anchor landmark coordinate, a structural property of the reference model at the landmark coordinate, and an alignment resolution associated with a first quantized distance, and, in accordance with a determination that the convergence metric satisfies a convergence heuristic and does not satisfy a resolution heuristic, associate the alignment resolution with a second quantized distance less than the first quantized distance, and modify a position of the anchor landmark coordinate based on the alignment resolution.

Example implementations also include a method of locating landmarks at a target object model by obtaining a target model associated with a target physical object, and a reference model associated with a reference physical object, the reference physical object including an anchor landmark coordinate and a secondary landmark coordinate, generating a reference warp associated with the anchor landmark coordinate of the reference model, generating a target warp associated with the anchor landmark coordinate of the target model, warping the target warp based on a topographical property of the target model, generating a secondary convergence heuristic based on a position of the secondary landmark coordinate relative to the reference warp, generating a secondary convergence metric based on a position of the secondary landmark coordinate relative to the target warp, and modifying a position of the secondary landmark coordinate relative to the reference warp and the warped target warp, in accordance with the secondary convergence metric and the secondary convergence heuristic.

BRIEF DESCRIPTION OF THE DRAWINGS

These and other aspects and features of the present implementations will become apparent to those ordinarily skilled in the art upon review of the following description of specific implementations in conjunction with the accompanying figures, wherein.

DETAILED DESCRIPTION

Figure 1A:
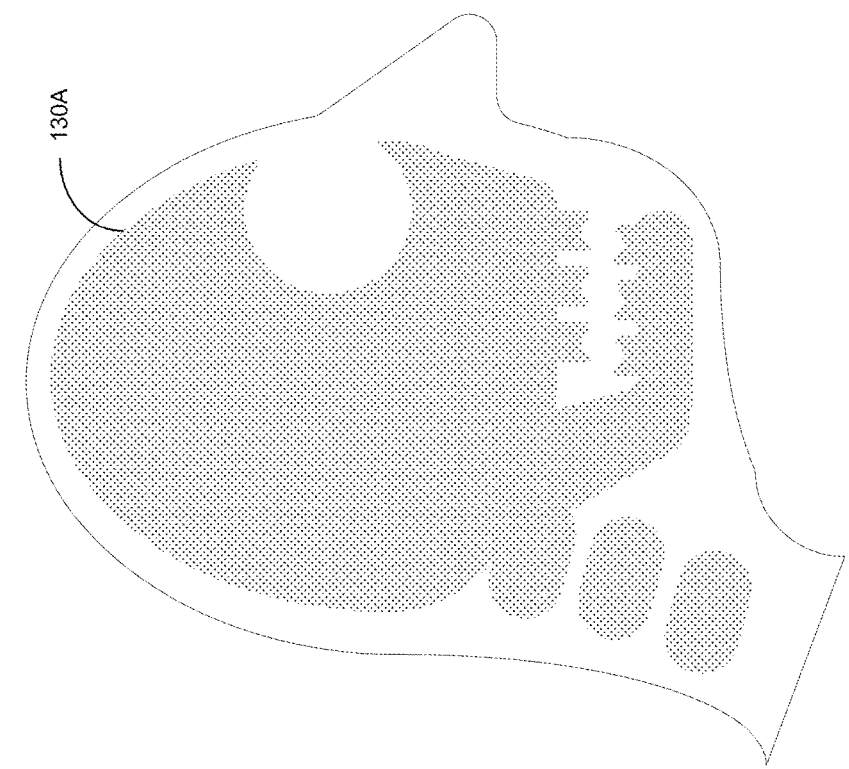
FIG. 1A illustrates an example first state of an example object model and an example first state of an example reference model, in accordance with present implementations.
Figure 1A:
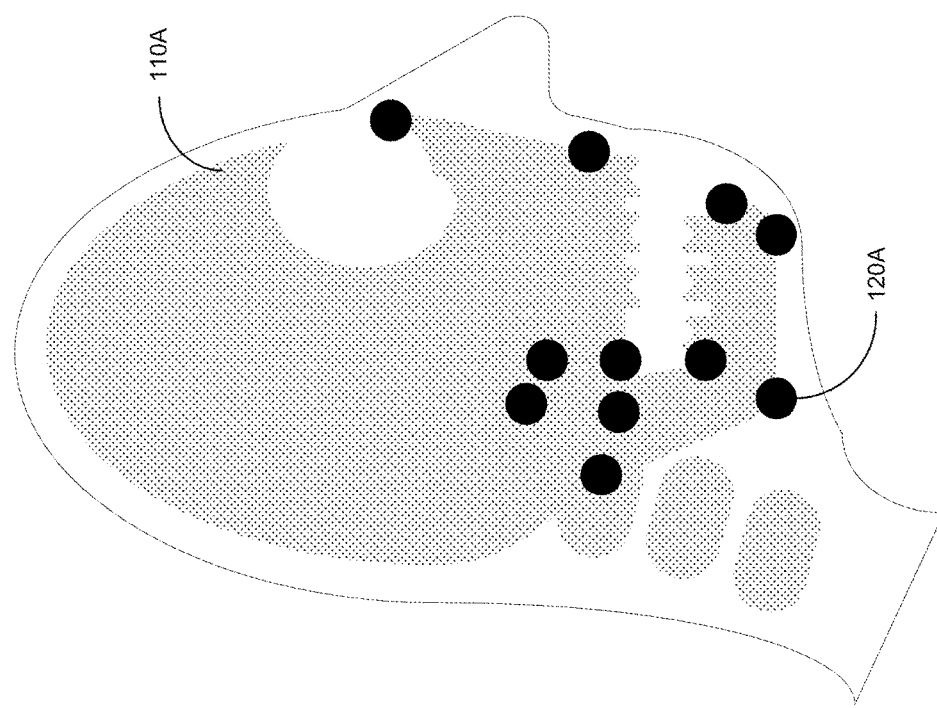

The present implementations will now be described in detail with reference to the drawings, which are provided as illustrative examples of the implementations so as to enable those skilled in the art to practice the implementations and alternatives apparent to those skilled in the art. Notably, the figures and examples below are not meant to limit the scope of the present implementations to a single implementation, but other implementations are possible by way of interchange of some or all of the described or illustrated elements. Moreover, where certain elements of the present implementations can be partially or fully implemented using known components, only those portions of such known components that are necessary for an understanding of the present implementations will be described, and detailed descriptions of other portions of such known components will be omitted so as not to obscure the present implementations. Implementations described as being implemented in software should not be limited thereto, but can include implementations implemented in hardware, or combinations of software and hardware, and vice-versa, as will be apparent to those skilled in the art, unless otherwise specified herein. In the present specification, an implementation showing a singular component should not be considered limiting; rather, the present disclosure is intended to encompass other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present implementations encompass present and future known equivalents to the known components referred to herein by way of illustration.

Landmark-based methods allow the creation of models enabling sophisticated assessment of image data. In biomedical imaging, anatomic landmarks enable the assessment of shape variation and to guide treatment plans and decision making ultimate leading to better patient outcomes. In non-medical applications, for example, feature points can be used to assess manufactured mechanical parts precision against designs. Regardless of application, precise manually placement and collection of landmark points is tedious and error prone. The automated landmark placement technology presented here greatly reduces error and time required to collect feature points resulting in a reliable framework for model creation.

Example implementations include a metric-based processing system including computational hardware and software operable to execute metric-based processes directed to placing landmarks at coordinates of models corresponding to physical structures. Specifically, example implementations are directed to applying metric-based analysis to locate landmark proximate to physical features associated with particular physical structures within a three-dimensional (3D) model or images from which it is derived. Landmarks identifying these physical features can be co-located with those features, and various image processing processes associated with various physical structures can be performed on regions of the 3D model to identify the physical structures likely to exist within those regions. As one example, a first set of landmarks can be placed by an iterative process within a target 3D model after having their initial location within the 3D model determined by a corresponding location within a reference model. Then, the landmarks can be repositioned iteratively in accordance with a metric-based iterative analysis until their location converges with a physical feature or representation thereof associated with the landmark. As another example, secondary landmarks can be placed by a computationally less expensive and optionally non-iterative process based on warps within the model connecting various landmarks within the model. In this example, the warp can first be placed in the target model based on corresponding reference points in a reference model, and warped where necessary to terminate at target landmarks whose locations may differ from their corresponding reference landmarks. Secondary landmarks can further be placed relative to the target warp, with their positions potentially modified in response to warping to the target space. Thus, in some implementations, a high degree of granularity in a 3D model for a patient can be achieved by locating landmarks by processes of varying computational complexity by various metric-based processors in a 3D model.

A warp can represent a transition from a reference to a target. It is to be understood that the warp can bridge a reference to a target by a transformation operation, a translation operation, a functional mapping, or the like, from one space to another. In some implementations, a warp can allow a bi-directional transformation operation, a translation operation, a functional mapping, or the like, between one space to another, but is not limited thereto.

It is to be understood that the metric-based processing can include machine learning processing based on metrics associated with landmark features, physical features, and the like. As one example, physical features can include dentition features. It is to be further understood that the metric-based processing can be executed by particular processors including transform processors and parallel processors operable in accordance with particular portions of or categories of machine learning processes governed by particular metrics at least disclosed herein. Thus, in some implementations, the metric-based processing includes a machine learning platform configured or constructed to execute particular processes based on the metrics and system disclosed herein.

FIG. 1A illustrates an example first state of an example object model and an example first state of an example reference model, in accordance with present implementations. As illustrated by way of example in FIG. 1A, an example first state 100 includes a reference model 110A associated with multiple reference landmarks 120A, and a target model 130A.

The reference model 110A is or includes a representation of a physical object, structure, or the like. In some implementations, the reference model 110A is or includes a three-dimensional (3D) model of a head, face, skull, and the like of a patient, including various maxillofacial and dentition structures. As one example, maxillofacial structures can include skull portions, skull plates, mandible portion, mandible portions, and the like, and ligaments, tendons, tissue, and the like associated therewith. As another example, dentition structures can include tooth structures, tooth surface topography, tooth cavities, tooth internal structures, tooth nerves, tooth enamel, and the like, and ligaments, tendons, tissue, and the like associated therewith. In some implementations, the reference model 110A is or includes a representation of a composite of physical 3D models corresponding to a particular common classification associated therewith. As one example, the reference model 110A can be based on multiple models each associated with a respective individual, where each of the multiple models is associated with a classification. As one example, a classification can be or include one or more of a gender, a demographic, an age, or the like. Thus, in some implementations, the reference model 110A is based on a composite of models representative of multiple individuals sharing a common classification.

The reference landmarks 120A include one or more coordinates relative to the reference model 110A and located at or proximate to a particular feature of the reference model 110A. In some implementations, the landmarks 120A are placed at a particular coordinate based on a determination that features of the reference model 110A correspond to a particular structural feature of the reference model 110A. In some implementations, a structural feature includes a shape, or the like detected in a 2D image or a 3D model. In some implementations, the landmarks 120 include landmark identifiers indicating a particular feature of a model associated with a patient. As one example, a landmark identifier can include a label or the like indicating that a corresponding landmark is located at or proximate to a particular feature or structure of the reference model 110A, such as a bone joint, curvature, protrusion, boundary, or the like. In some implementations, the reference landmarks 120A are based on a composite of landmarks associated with multiple models each associated with a respective individual, where each of the multiple models is associated with a classification. The reference landmarks 120A can each be derived from an aggregation of landmarks corresponding to a particular location or landmark identifier. As one example, a reference landmark of the reference landmarks 120A, corresponding to the bridge of a nose, can have a coordinate or set of coordinates averaged, or the like, from a plurality of landmarks associated with models for multiple individuals and also corresponding to the bridge of a nose.

The target model 130A is or includes a representation of a physical object, structure, or the like. In some implementations, the reference model 110A is or includes a three-dimensional (3D) model of a head, face, skull, and the like of a patient, including various maxillofacial and dentition structures. In some implementations, the target model 130A represents a model of a patient obtained by a biomedical imaging system and lacks landmarks associated therewith. As one example, medical imaging system can include magnetic resonance imaging (MRI), X-ray imaging, computerized tomography (CT) scans, computerized axial tomography (CAT) scans, and the like.

Figure 1B:
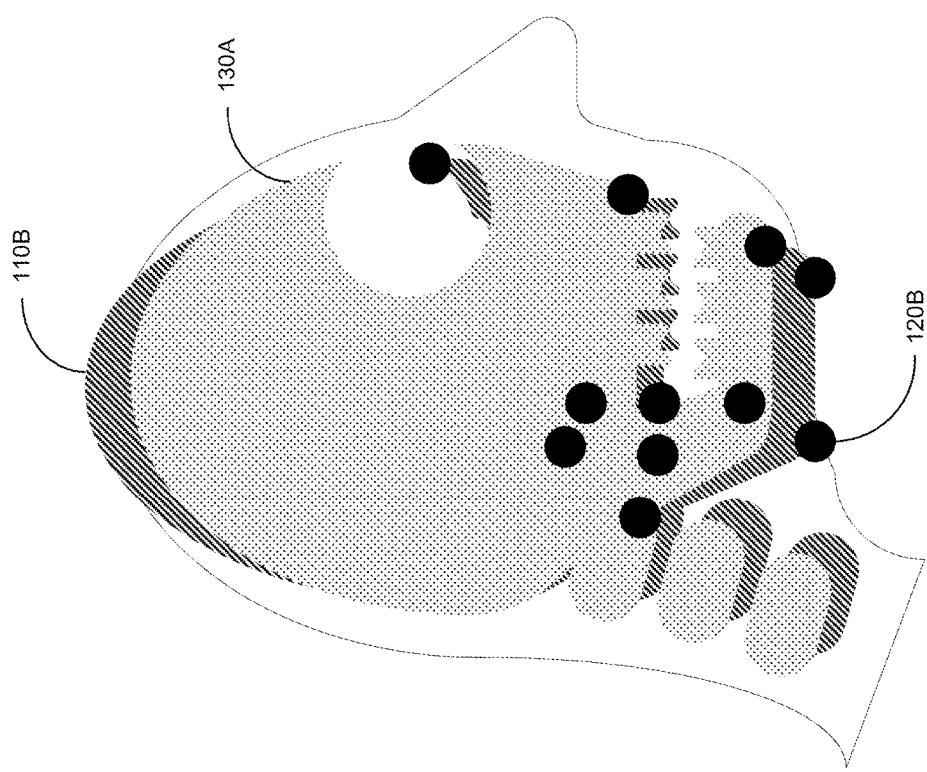
FIG. 1B illustrates an example second state of an example object model and an example second state of an example reference model, in accordance with present implementations.

FIG. 1B illustrates an example second state of an example object model and an example second state of an example reference model, in accordance with present implementations. As illustrated by way of example in FIG. 1B, an example second state 100B includes a transposed reference model 110B, the target model 130A, and target landmarks 120B.

The transposed reference model 110B corresponds to the reference model 110A and is transposed to align with the target model 130A. In some implementations, the transposed reference model 110B is transposed to align with the target model 130A by one or more geometric operations relative to one or more axes common to the reference model 110A and the target model 130A. As one example, an axis can be along a transverse plane, a coronal plane, or a sagittal plane dividing or bisecting the 3D model. Thus, in some implementations, the reference model 110A and the target model 130A are placed in coarse alignment in accordance with one or more axes and planes. The target landmarks 120B correspond to the reference landmarks 120B and are associated with the target model 130A. In some implementations, the target landmarks 120B are associated with the target model 130A in response to transposition of the reference model 110A to the transposed reference model 110B relative to the target model 130A. Thus, the target landmarks 120B are in coarse alignment with the target model 130A in response to the transposition of the reference model 110A including the reference landmarks 120A.

Figure 1C:
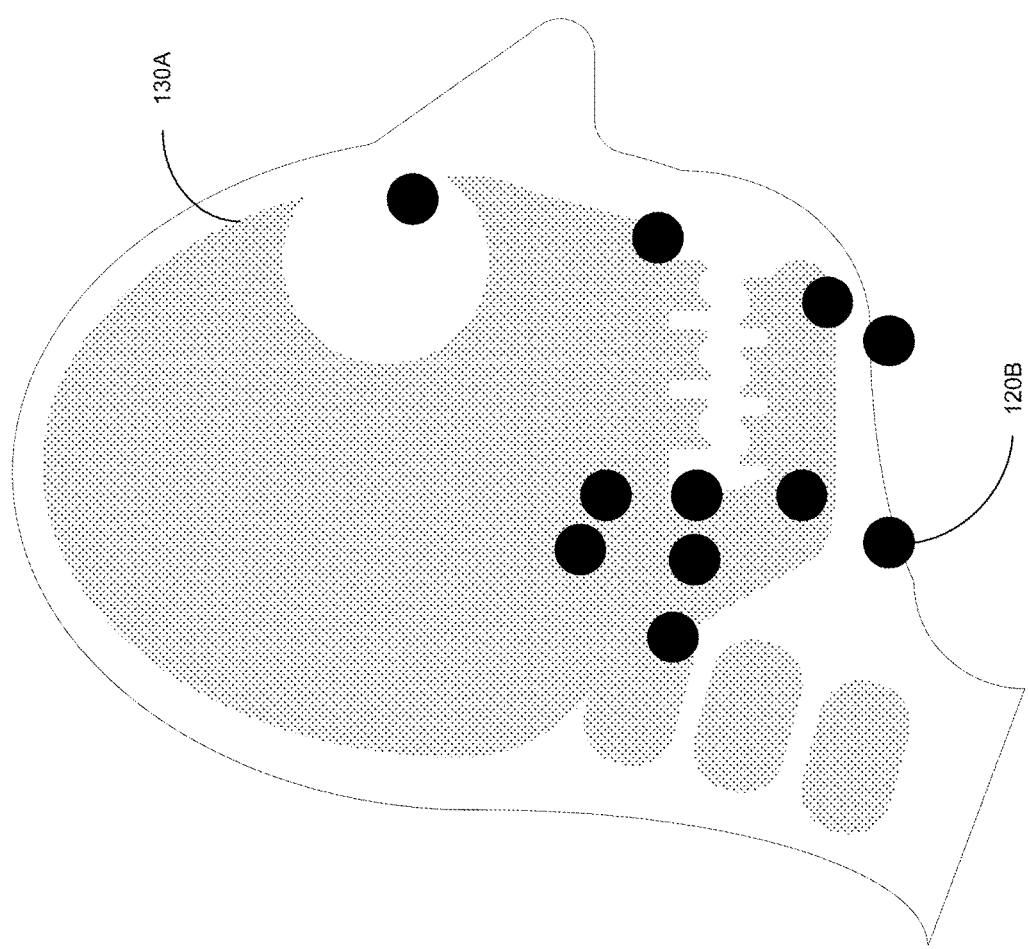
FIG. 1C illustrates an example third state of an example object model, in accordance with present implementations.

FIG. 1C illustrates an example third state of an example object model, in accordance with present implementations. As illustrated by way of example in FIG. 1C, an example third state 100C includes the target model 130A and the target landmarks 130B. In some implementations, the transposed reference model 110B is subtracted, remove, blocked, discarded or the like after the target landmarks 120B are associated with the target model 120B. Thus, in some implementations, the third state 100C includes a target model 130A including multiple target landmarks 120B in coarse alignment therewith, in response to a transposition process with the reference model 110A including multiple reference landmarks 120A.

Figure 2A:
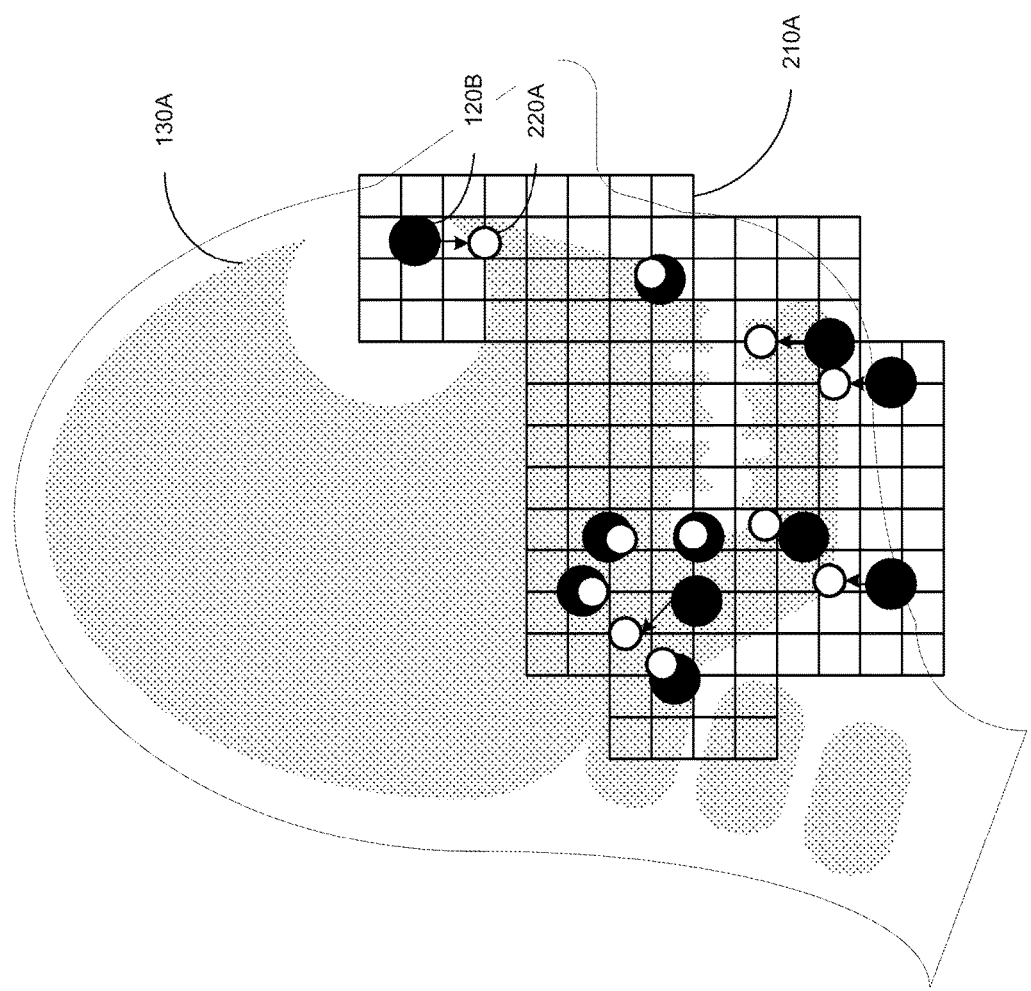
FIG. 2A illustrates an example fourth state of an example object model, in accordance with present implementations.

FIG. 2A illustrates an example fourth state of an example object model, in accordance with present implementations. As illustrated by way of example in FIG. 2A, an example fourth state 200A includes the target model 130A, the target landmarks 120B, a first alignment resolution coordinate space 210A, and refined landmarks 220A.

The first alignment resolution coordinate space 210A is disposed within the coordinate space of the target model 130A, and defines a first resolution at which to further align the coarsely aligned target landmarks 120B. In some implementations, the first resolution has a first minimum distance and is conducted during a first alignment refinement iteration. In some implementations, the first minimum distance associated with the first alignment resolution coordinate space 210A is greater than any minimum distance associated with any alignment resolution coordinate space during any subsequent iteration. Thus, in some implementations, the resolution decreases as the number of iterations increases.

The refined landmarks 220A are obtained based on a refinement process to align the target landmarks 120B with particular features of the target model 130A proximate to individual ones of the target landmarks 120B, and in alignment with the first alignment resolution coordinate space 210A. In some implementations, the refined landmarks 220A are obtained by modifying corresponding positions of the target landmarks 120B in accordance with one or more convergence metrics. In some implementations, the refined landmarks 220A are obtained by generating the refined landmarks 220A based on corresponding positions of the target landmarks 120B and one or more convergence metrics, and subsequently discarding the target landmarks 120B.

Figure 2B:
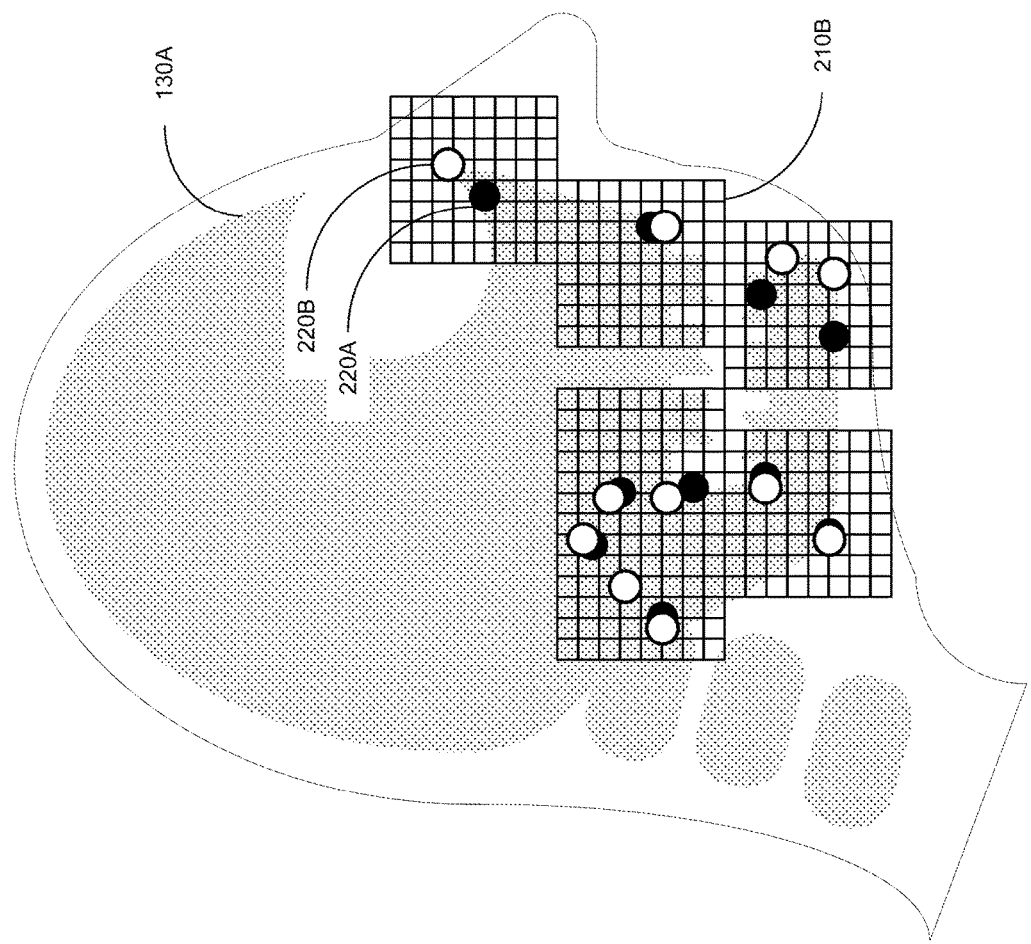
FIG. 2B illustrates an example fifth state of an example object model, in accordance with present implementations.

FIG. 2B illustrates an example fifth state of an example object model, in accordance with present implementations. As illustrated by way of example in FIG. 2B, an example fifth state 200B includes the target model 130A, the refined landmarks 220A, a second alignment resolution coordinate space 210B, and refined landmarks 220B.

The second alignment resolution coordinate space 210B is disposed within the coordinate space of the target model 130A, and defines a second resolution at which to further align the refined landmarks 220A. In some implementations, the second resolution has a second minimum distance and is conducted during a second alignment refinement iteration. In some implementations, the second minimum distance associated with the second alignment resolution coordinate space 210B is greater than any minimum distance associated with any alignment resolution coordinate space during any subsequent iteration, and less than the first minimum distance. Thus, in some implementations, the resolution further decreases as the number of iterations increases. It is to be understood that resolution can decrease over any number of iterations, and is not limited to reduction at each iteration of an alignment refinement. It is to be further understood that that the alignment resolution can increase for various iterations and under various circumstances. As one example, an alignment resolution can increase if a landmarks reaches convergence at a local minimum. In this example, the alignment resolution can increase to attempt to remove the landmark of the local minimum and toward an absolute minimum of convergence.

The refined landmarks 220B are obtained based on a refinement process to align the refined landmarks 220A with particular features of the target model 130A proximate to individual ones of the refined landmarks 220A, and in alignment with the second alignment resolution coordinate space 210B. In some implementations, the refined landmarks 220B are obtained by modifying corresponding positions of the refined landmarks 220A in accordance with one or more convergence metrics. In some implementations, the refined landmarks 220B are obtained by generating the refined landmarks 220B based on corresponding positions of the refined landmarks 220A and one or more convergence metrics, and subsequently discarding the refined landmarks 220A.

Figure 3A:
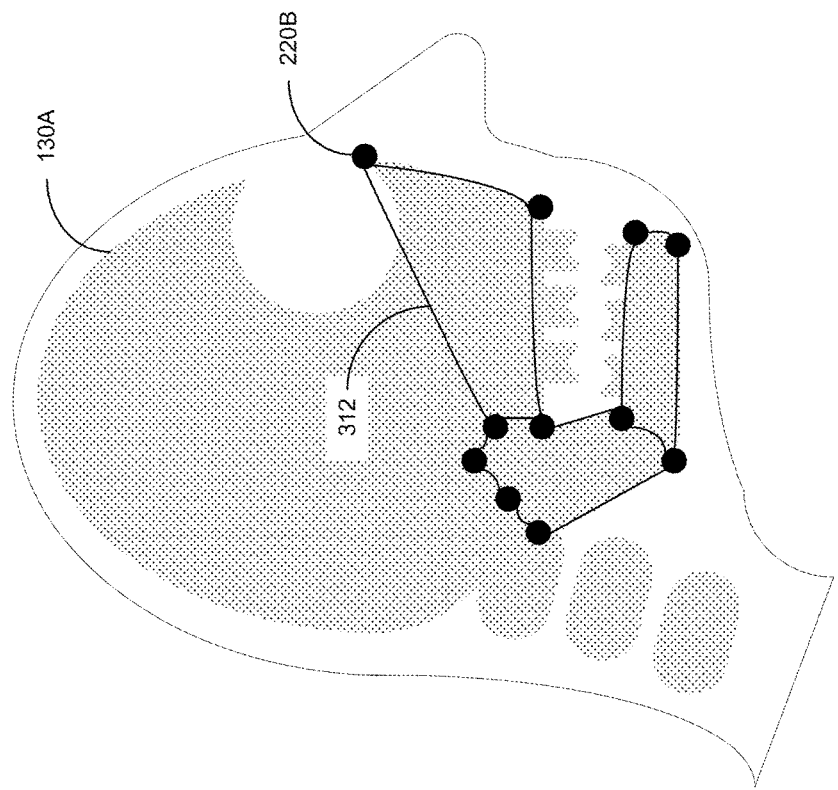
FIG. 3A illustrates an example sixth state of an example object model and an example third state of an example reference model, in accordance with present implementations.
Figure 3A:
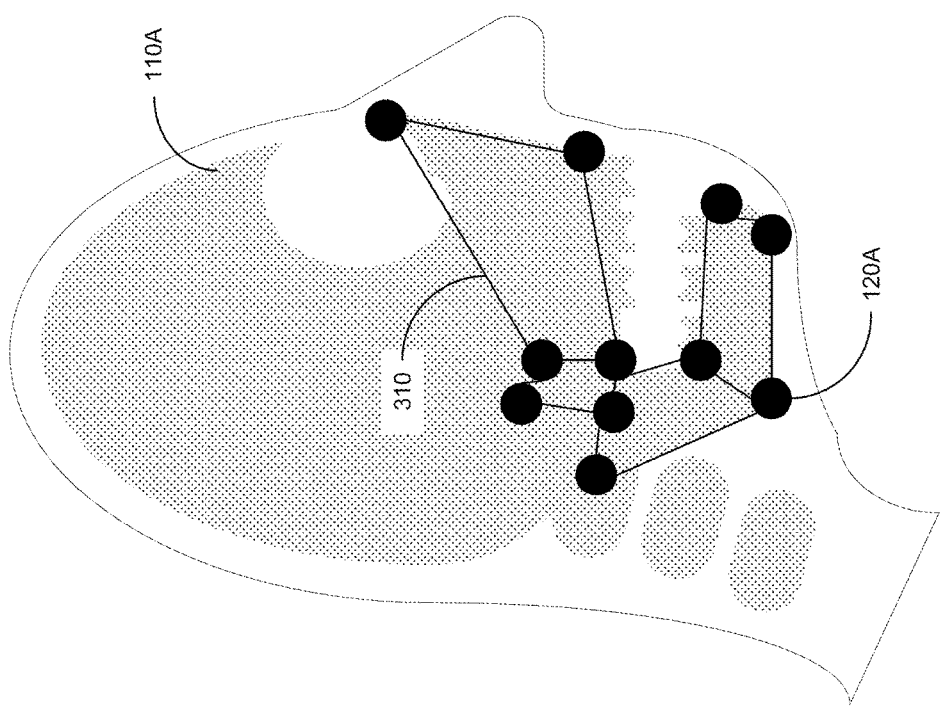

FIG. 3A illustrates an example sixth state of an example object model and an example third state of an example reference model, in accordance with present implementations. As illustrated by way of example in FIG. 3A, an example sixth state 300A includes the reference model 110A, the reference landmarks 120A, the target model 130A, the refined landmarks 220B, reference warps 310, and target warps 312.

The reference warps 310 include corresponding transformation relationships, translation relationships, or the like associated with reference landmarks 120A. In some implementations, the reference warps 310 represent a coordinate space orientation of reference landmarks 120A in a first coordinate space prior to transformation, translation, or the like. It is to be understood that the reference warps 310 can be provided to illustrate a coordinate space associated with reference landmarks 120A, and are not required for transformation, translation, or the like, between coordinate spaces.

The target warps 312 include corresponding transformation relationships, translation relationships, or the like associated with target landmarks 120B or refined landmarks 220B. In some implementations, the target warps 312 represent a coordinate space orientation of target landmarks 120B or refined landmarks 220B in a second coordinate space after transformation, translation, or the like from a first coordinate space. It is to be understood that the target warps 312 can be provided to illustrate a coordinate space associated with target landmarks 120B or refined landmarks 220B, and are not required for transformation, translation, or the like, between coordinate spaces.

Figure 3B:
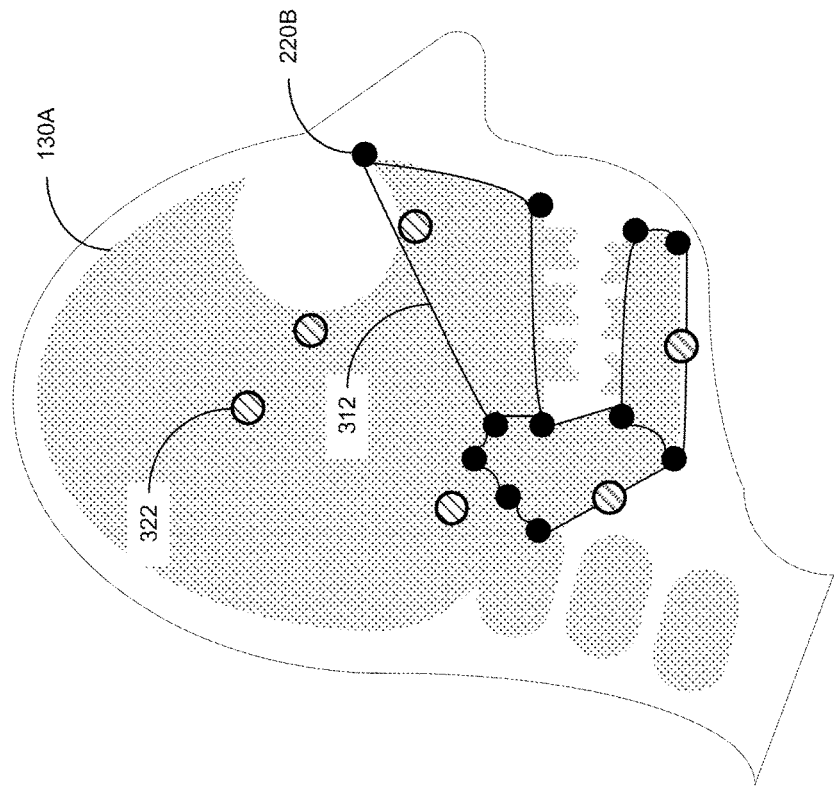
FIG. 3B illustrates an example seventh state of an example object model and an example fourth state of an example reference model, in accordance with present implementations.
Figure 3B:
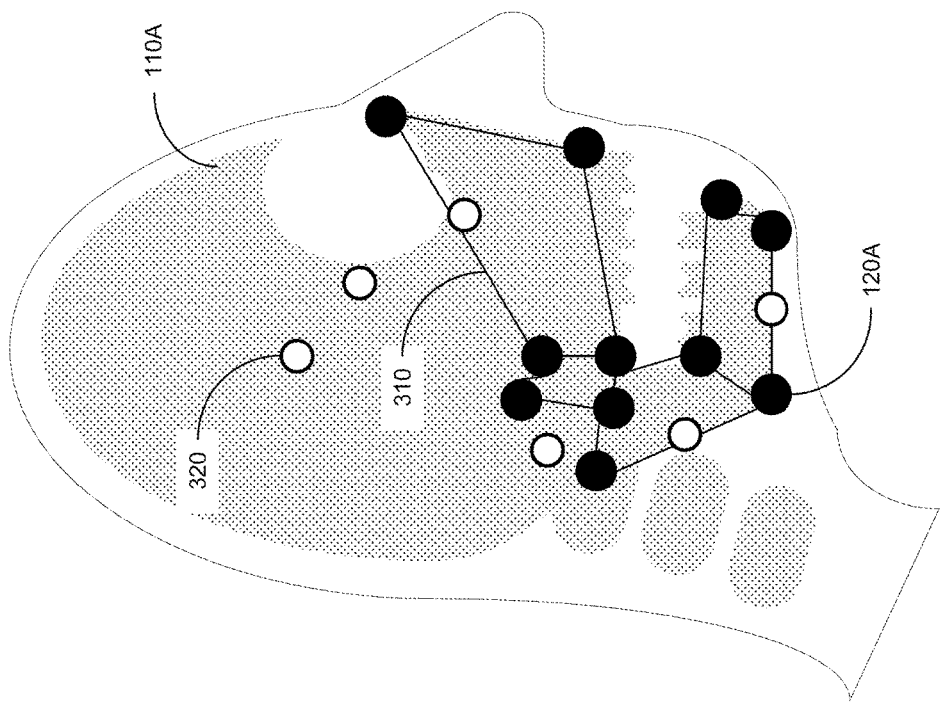

FIG. 3B illustrates an example seventh state of an example object model and an example fourth state of an example reference model, in accordance with present implementations. As illustrated by way of example in FIG. 3B, an example seventh state includes the reference model 110A, the reference landmarks 120A, the reference warps 310, the target model 130A, the target landmarks 220B, the target warps 312, secondary reference landmarks 320, and secondary target landmarks 322.

The secondary reference landmarks 320 correspond in type, structure and the like, to the reference landmarks 120A. In some implementations, the secondary reference landmarks 320 include a relative position relationship with one or more particular reference warps 310, thus allowing the secondary reference landmarks 320 to be defined both by absolute coordinates of the coordinate system of the reference model 120A and by relative coordinates respective to the reference warps 310. In some implementations, the secondary reference landmarks 320 are excluded from an alignment and refinement process associated with the reference landmarks 120A. This exclusion can reduce the amount of noise introduced or the computational resources required to place landmarks by a computationally expensive refinement process and increase efficiency and speed of generation of a complete target landmark model based on a complete reference landmark model including both reference landmarks 120A and secondary reference landmarks 320. As one example, a reference model 110A can include under 100 reference landmarks 120A and thousands of secondary reference landmarks 320.

The secondary target landmarks 322 correspond in type, structure and the like, to the target landmarks 220B. In some implementations, the secondary target landmarks 322 are associated with the target model 130A in response to transposition of the secondary reference landmarks 320 to the target model 130A relative to the target warps 312, and can have their absolute position differ from the absolute position of their respective secondary reference landmarks 320 in response to the warping of the target warps 312 relative to the reference warps 310. As one example, a secondary target landmark can be shifted downward relative to its corresponding secondary reference landmark when its corresponding target warp is warped downward relative to its corresponding reference warp. Thus, the secondary target landmarks 322 are in relative alignment with the target warps 312. In some implementations, the secondary target landmarks 322 can be further refined in accordance with FIG. 2B.

Figure 4:
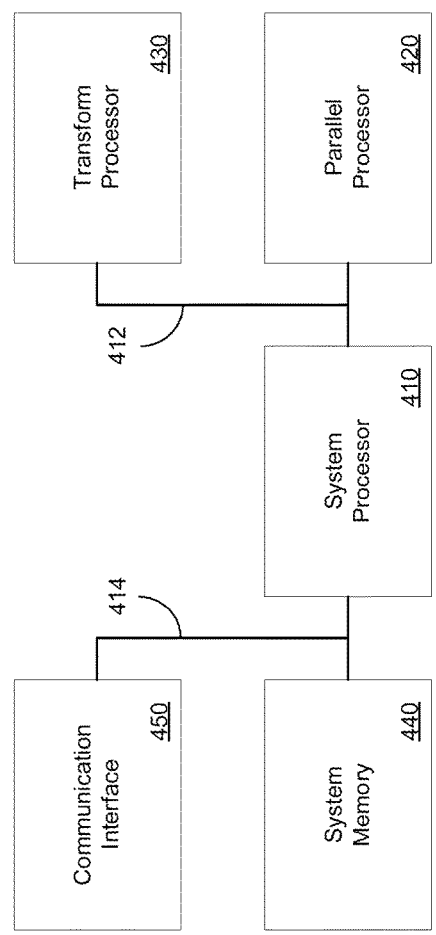
FIG. 4 illustrates an example processing system, in accordance with present implementations.

FIG. 4 illustrates an example processing system, in accordance with present implementations. As illustrated by way of example in FIG. 4, an example processing system 400 includes a system processor 410, a parallel processor 420, a transform processor 430, a system memory 440, and a communication interface 450. In some implementations, at least one of the example processing system 400 and the system processor 410 includes a processor bus 412 and a system bus 414.

The system processor 410 is operable to execute one or more instructions. In some implementations, the instructions are associated with at least one of the system memory 440 and the communication interface 450. In some implementations, the system processor 410 is an electronic processor, an integrated circuit, or the like including one or more of digital logic, analog logic, digital sensors, analog sensors, communication buses, volatile memory, nonvolatile memory, and the like. In some implementations, the system processor 410 includes but is not limited to, at least one microcontroller unit (MCU), microprocessor unit (MPU), central processing unit (CPU), graphics processing unit (GPU), physics processing unit (PPU), embedded controller (EC), or the like. In some implementations, the system processor 410 includes a memory operable to store or storing one or more instructions for operating components of the system processor 410 and operating components operably coupled to the system processor 410. In some implementations, the one or more instructions include at least one of firmware, software, hardware, operating systems, embedded operating systems, and the like.

The processor bus 412 is operable to communicate one or more instructions, signals, conditions, states, or the like between one or more of the system processor 410, the parallel processor 420, and the transform processor 430. In some implementations, the processor bus 412 includes one or more digital, analog, or like communication channels, lines, traces, or the like. It is to be understood that any electrical, electronic, or like devices, or components associated with the system bus 414 can also be associated with, integrated with, integrable with, supplemented by, complemented by, or the like, the system processor 410 or any component thereof.

The system bus 414 is operable to communicate one or more instructions, signals, conditions, states, or the like between one or more of the system processor 410, the system memory 440, and the communication interface 450. In some implementations, the system bus 414 includes one or more digital, analog, or like communication channels, lines, traces, or the like. It is to be understood that any electrical, electronic, or like devices, or components associated with the system bus 414 can also be associated with, integrated with, integrable with, supplemented by, complemented by, or the like, the system processor 410 or any component thereof.

The parallel processor 420 is operable to execute one or more instructions concurrently, simultaneously, or the like. In some implementations, the parallel processor 420 is operable to execute one or more instructions in a parallelized order in accordance with one or more parallelized instruction parameters. In some implementations, parallelized instruction parameters include one or more sets, groups, ranges, types, or the like, associated with various instructions. In some implementations, the parallel processor 420 includes one or more execution cores variously associated with various instructions. In some implementations, the parallel processor 420 includes one or more execution cores variously associated with various instruction types or the like. In some implementations, the parallel processor 420 is an electronic processor, an integrated circuit, or the like including one or more of digital logic, analog logic, communication buses, volatile memory, nonvolatile memory, and the like. In some implementations, the parallel processor 420 includes but is not limited to, at least one graphics processing unit (GPU), physics processing unit (PPU), embedded controller (EC), gate array, programmable gate array (PGA), field-programmable gate array (FPGA), application-specific integrated circuit (ASIC), or the like. It is to be understood that any electrical, electronic, or like devices, or components associated with the parallel processor 420 can also be associated with, integrated with, integrable with, supplemented by, complemented by, or the like, the system processor 410 or any component thereof.

Figure 5:
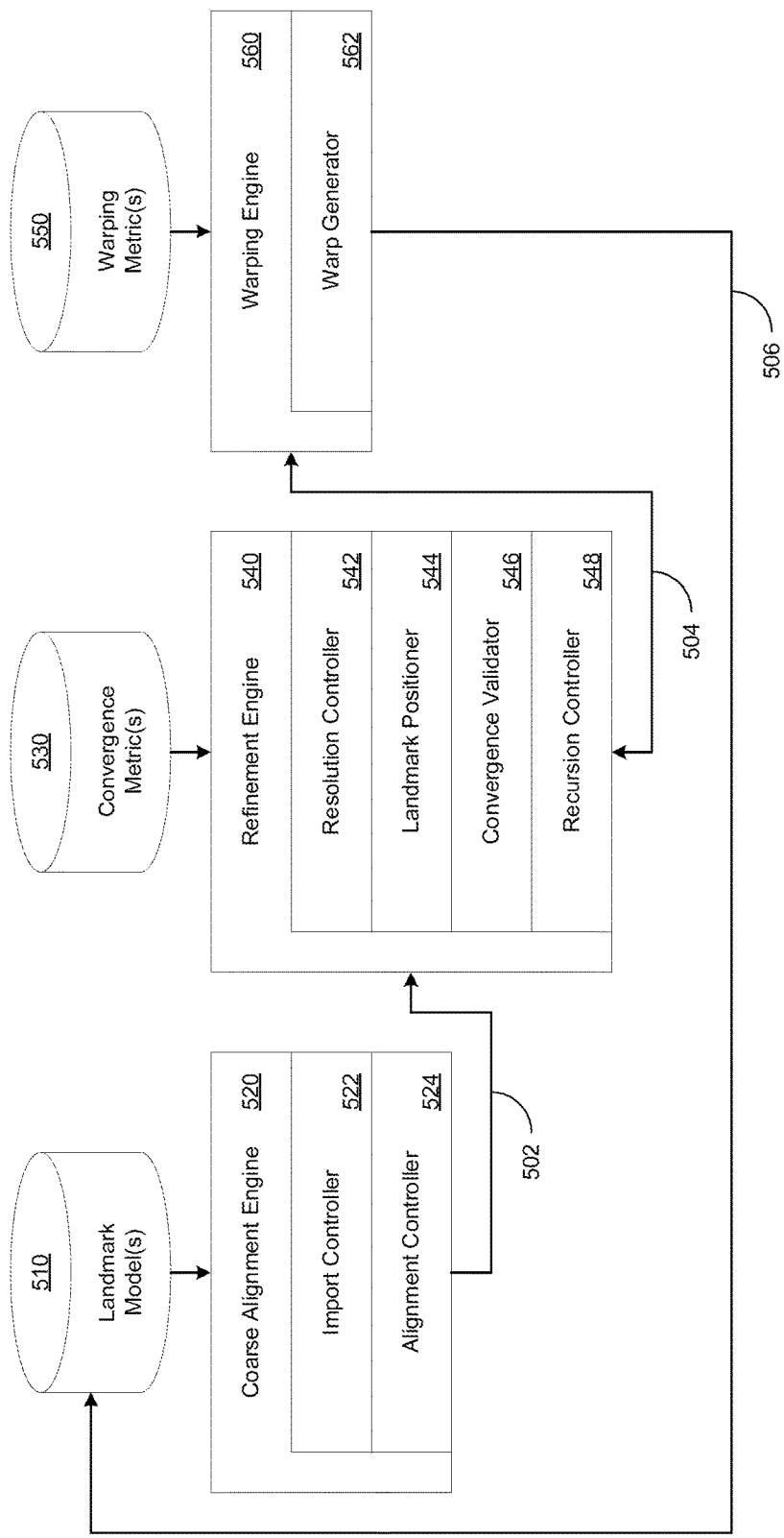
FIG. 5 illustrates an example computing system, in accordance with present implementations.

In some implementations, various cores of the parallel processor 420 are associated with one or more parallelizable operations in accordance with one or more metrics, engines, models, and the like, of the example computing system of FIG. 5. As one example, parallelizable operations include processing portions of an image, video, waveform, audio waveform, processor thread, one or more layers of a learning model, one or more metrics of a learning model, one or more models of a learning system, and the like. In some implementations, a predetermined number or predetermined set of one or more particular cores of the parallel processor 420 are associated exclusively with one or more distinct sets of corresponding metrics, engines, models, and the like, of the example computing system of FIG. 5. As one example, a first core of the parallel processor 420 can be assigned to, associated with, configured to, fabricated to, or the like, execute one engine of the example computing system of FIG. 5. In this example, a second core of the parallel processor 420 can also be assigned to, associated with, configured to, fabricated to, or the like, execute another engine of the example computing system of FIG. 5. Thus, in some implementations, the parallel processor 420 is configured to parallelize execution across one or more metrics, engines, models, and the like, of the example computing system of FIG. 5.

Similarly, in some implementations, a predetermined number or predetermined set of one or more particular cores of the parallel processor 420 are associated collectively with corresponding metrics, engines, models, and the like, of the example computing system of FIG. 5. As one example, a first plurality of cores of the parallel processor can be assigned to, associated with, configured to, fabricated to, or the like, execute one engine of the example computing system of FIG. 5. In this example, a second plurality of cores of the parallel processor can also be assigned to, associated with, configured to, fabricated to, or the like, execute another engine of the example computing system of FIG. 5. Thus, in some implementations, the parallel processor 420 is configured to parallelize execution within one or more metrics, engines, models, and the like, of the example computing system of FIG. 5.

The transform processor 430 is operable to execute one or more instructions associated with one or more predetermined transformation processes. As one example, transformation processes include Fourier transforms, matrix operations, calculus operations, combinatoric operations, trigonometric operations, geometric operations, encoding operations, decoding operations, compression operations, decompression operations, image processing operations, audio processing operations, and the like. In some implementations, the transform processor 430 is operable to execute one or more transformation processes in accordance with one or more transformation instruction parameters. In some implementations, transformation instruction parameters include one or more instructions associating the transform processor 430 with one or more predetermined transformation processes. In some implementations, the transform processor 430 includes one or more transformation processes. Alternatively, in some implementations, the transform processor 430 is a plurality of transform processor 430 associated with various predetermined transformation processes. Alternatively, in some implementations, the transform processor 430 includes a plurality of transformation processing cores each associated with, configured to execute, fabricated to execute, or the like, a predetermined transformation process. In some implementations, the parallel processor 420 is an electronic processor, an integrated circuit, or the like including one or more of digital logic, analog logic, communication buses, volatile memory, nonvolatile memory, and the like. In some implementations, the parallel processor 420 includes but is not limited to, at least one graphics processing unit (GPU), physics processing unit (PPU), embedded controller (EC), gate array, programmable gate array (PGA), field-programmable gate array (FPGA), application-specific integrated circuit (ASIC), or the like. It is to be understood that any electrical, electronic, or like devices, or components associated with the transform processor 430 can also be associated with, integrated with, integrable with, supplemented by, complemented by, or the like, the system processor 410 or any component thereof.

In some implementations, the transform processor 430 is associated with one or more predetermined transform processes in accordance with one or more metrics, engines, models, and the like, of the example computing system of FIG. 5. In some implementations, a predetermined transform process of the transform processor 430 is associated with one or more corresponding metrics, engines, models, and the like, of the example computing system of FIG. 5. As one example, the transform processor 430 can be assigned to, associated with, configured to, fabricated to, or the like, execute one matrix operation associated with one or more engines, metrics, models, or the like, of the example computing system of FIG. 5. As another example, the transform processor 430 can alternatively be assigned to, associated with, configured to, fabricated to, or the like, execute another matrix operation associated with one or more engines, metrics, models, or the like, of the example computing system of FIG. 5. Thus, in some implementations, the transform processor 430 is configured to centralize, optimize, coordinate, or the like, execution of a transform process across one or more metrics, engines, models, and the like, of the example computing system of FIG. 5. In some implementations, the transform processor is fabricated to, configured to, or the like, execute a particular transform process with at least one of a minimum physical logic footprint, logic complexity, heat expenditure, heat generation, power consumption, and the like, with respect to at least one metrics, engines, models, and the like, of the example computing system of FIG. 5.

The system memory 440 is operable to store data associated with the example processing system 400. In some implementations, the system memory 440 includes ones or more hardware memory devices for storing binary data, digital data, or the like. In some implementations, the system memory 440 includes one or more electrical components, electronic components, programmable electronic components, reprogrammable electronic components, integrated circuits, semiconductor devices, flip flops, arithmetic units, or the like. In some implementations, the system memory 440 includes at least one of a non-volatile memory device, a solid-state memory device, a flash memory device, and a NAND memory device. In some implementations, the system memory 440 includes one or more addressable memory regions disposed on one or more physical memory arrays. In some implementations, a physical memory array includes a NAND gate array disposed on a particular semiconductor device, integrated circuit device, printed circuit board device, and the like.

The communication interface 450 is operable to communicatively couple the system processor 410 to an external device. In some implementations, an external device includes but is not limited to a smartphone, mobile device, wearable mobile device, tablet computer, desktop computer, laptop computer, cloud server, local server, and the like. In some implementations, the communication interface 450 is operable to communicate one or more instructions, signals, conditions, states, or the like between one or more of the system processor 410 and the external device. In some implementations, the communication interface 450 includes one or more digital, analog, or like communication channels, lines, traces, or the like. As one example, the communication interface 450 is or includes at least one serial or parallel communication line among multiple communication lines of a communication interface. In some implementations, the communication interface 450 is or includes one or more wireless communication devices, systems, protocols, interfaces, or the like. In some implementations, the communication interface 450 includes one or more logical or electronic devices including but not limited to integrated circuits, logic gates, flip flops, gate arrays, programmable gate arrays, and the like. In some implementations, the communication interface 450 includes ones or more telecommunication devices including but not limited to antennas, transceivers, packetizers, wired interface ports, and the like. It is to be understood that any electrical, electronic, or like devices, or components associated with the communication interface 450 can also be associated with, integrated with, integrable with, replaced by, supplemented by, complemented by, or the like, the system processor 410 or any component thereof.

FIG. 5 illustrates an example computing system, in accordance with present implementations. As illustrated by way of example in FIG. 5, an example computing system 500 includes a landmark model database 510, a coarse alignment engine 520, a convergence metric database 530, a refinement engine 540, a warping metric database 550, and a warping engine 560. It is to be understood that one or more of the engines and databases can be located, stored, or the like, in a single logical or physical block or areas of the system memory 440, or distributed at or across multiple physical or virtual devices, or associated with corresponding dedicated devices.

The landmark model database 510 includes at least one landmark model associated with at least one 3D model. In some implementations, the landmark model is associated with a reference model including multiple reference landmarks. In some implementations, a reference model includes a 3D model including one or more landmarks and associated with a reference classification. In some implementations, a reference classification includes but is not limited to age, gender, demographics, and the like. As one example, the landmark model database 510 can include a reference model including reference landmarks located at or proximate to features of a male between the ages of 5 and 10 years, and can include a separate reference model including reference landmarks located at or proximate to features of a female between the ages of 45 and 65 years. Thus, in some implementations, the landmark model database 510 includes multiple reference models each respectively associated with one or more classifications. It is to be understood that the classification or classifications associated with each reference model can be predetermined and can include an arbitrary number of classifications of unlimited types.

The coarse alignment engine 520 is operable to place one or more landmarks associated with a reference model onto a target model at a first, less granular level of specificity. In some implementations, the coarse alignment engine includes one or more sequential or parallel processes to translate a landmark from a reference model to a corresponding coordinate position at a target model. Coarse alignment can include alignment at particular coordinates common to a coordinate system associated with a reference model and a target model. As one example, a reference landmark at a reference model described in three dimensions by a Cartesian coordinate system can be placed at those same three Cartesian coordinates within the coordinate space associated with the target model. Thus, in some implementations, the coarse alignment engine 520 translates landmarks from a reference model to a target model based on coordinates associated with particular reference landmarks. In some implementations, the coarse alignment engine 520 includes at least one of an import controller 522 and an alignment controller 524.

The import controller 522 is operable to import landmarks and warps associated with at least one particular reference model to a target model. In some implementations, the import controller 522 is operable to obtain one or more classifications associated with a target model, and to obtain at least one reference model corresponding to the obtained classifications. As one example, the import controller 522 can obtain classifications associated with a target model including a reference model corresponding to a male and to an individual having an age of 10 years, and can obtain a reference model associated with the corresponding classifications. In some implementations, the import controller 522 can obtain a reference model associated with a range of classifications.

The alignment controller 524 is operable to place reference landmarks associated with the reference model onto a target model. In some implementations, the alignment controller 524 includes a coordinate processor or the like including at least one cache, buffer, or the like, to copy or the like a plurality of reference landmarks from the reference model to the target model. In some implementations, the alignment controller 524 generates a landmark index comprising one or more vectors, matrices, or the like each defining a set of reference landmarks associated with the target model and derived from a corresponding set associated with the reference model. By placing reference landmarks onto a target model from a reference model matching a classification of the target model, the reference landmarks can be located proximate to or at structural features common to both the reference model and the target model. In some implementations, the alignment controller 524 includes a model communication channel 502.

The model communication channel 502 is operable to transmit the target model including the reference landmarks to the refinement engine 540. The model communication channel 502 is operable to communicatively couple the coarse alignment controller 520 to the refinement engine 540. In some implementations, the model communication channel 502 is operable to communicate one or more instructions, signals, conditions, states, or the like between one or more of the coarse alignment controller 520 and the refinement engine 540. In some implementations, the model communication channel 502 includes one or more logical, digital, analog, or like communication channels, lines, traces, or the like. In some implementations, the model communication channel 502 includes a logical address to a header, interface, application programming interface, PUT interface, POST interface, or the like, associated with the refinement engine.

The convergence metric database 530 includes one or more convergence metrics indicating whether a landmark is placed at an optimal location with respect to a particular features of a target model. In some implementations, the convergence metrics includes one or more vectors indicating a correspondence between an expected structure within a predetermined range of a landmark at the reference model and an actual structure within the predetermined range of the landmark at the target model. In some implementations, the convergence metric database 530 includes one or more convergence metrics corresponding specifically to particular structures, features, or the like. As one example, the convergence metric database 530 can include a first set of one or more convergence metrics operable to quantify correspondence of a landmark to a particular maxillofacial feature at a particular local area of a maxillofacial region. As another example, the convergence metric database 530 can include a second set of one or more convergence metrics operable to quantify correspondence of a landmark to another particular maxillofacial feature at a another particular local area of a maxillofacial region.

In some implementations, the convergence metric database 530 is or includes one or more vector-based transformation operations based on a particular bit-length of the vector corresponding to a distance within a particular coordinate space. In some implementations, the bit length corresponds to a particular range at a predetermined resolution within the coordinate space. As one example, a bit length can correspond to a first distance at a first resolution, or a second distance half as long as the first distance at a second resolution twice as high as the first resolution. It is to be understood that the bit length, range, and resolution can include any linear or nonlinear relationship. It is to be further understood that transformation data structures other than or in addition to vectors can comprise the convergence metric database 530.

The refinement engine 540 is operable to modify one or more landmark positions in accordance with one or more convergence metrics. In some implementations, the refinement engine 540 is operable to execute one or more transformation processes by the transform processor 430. In some implementations, the refinement engine 540 is operable to execute one or more parallel processes by the parallel processor 430. In some implementations, the refinement engine 540 iterates placement of landmarks until determining that the particular landmark has a reached convergence position according to one or more convergence metrics. In some implementations, the refinement engine 540 includes at least one of a resolution controller 542, a landmark positioner 544, a convergence validator 546, and a recursion controller 548.

The resolution controller 542 is operable to modify a resolution associated with a refinement process and corresponding to a granularity of a coordinate space surrounding a particular landmark. In some implementations, the resolution controller 542 includes one or more processes to transform portions of a target model to correspond to a particular resolution. As one example, the resolution controller 542 can transform one or more portions of a target model by averaging all points within the target model within a particular resolution area, volume, or the like. In this example, the resolution controller 542 can average luminosity, chroma, or the like of all points within a first resolution distance of a particular landmark, and can average luminosity, chroma, or the like of all points beyond a first resolution distance of a particular landmark and within a second resolution distance of the particular landmark. Thus, in some implementations, the resolution controller 542 can simplify a target model to an arbitrary resolution granularity. As one example, resolution granularity can be defined as distance, pixel distance, pixel number, voxel distance, voxel number, vector distance, or the like, associated with any coordinate system.

The landmark positioner 544 is operable to locate one or more landmarks at one or more coordinate positions within a coordinate space associated with a target model, and to modify a coordinate position or any portion thereof. In some implementations, the landmark positioner 544 places landmarks at points of a coordinate system having a minimum distance defined by a resolution of the resolution controller 542, and the landmark positioner 544 is operable to modify distances between points, angles, or the like of a coordinate system responsive to a resolution determined by the resolution controller 542. In some implementations, the landmark positioner 544 is operable to locate one or more landmarks at one or more coordinate positions within a coordinate space relative to a warp of a target model, and to modify a coordinate position or any portion thereof relative to the warp.

The convergence validator 546 is operable to determine whether a particular landmark reaches a convergence point with respect to a target model based on one or more convergence metrics. In some implementations, the convergence validator 546 is or include a machine learning engine operable to obtain one or more convergence metrics from the convergence metric database 530 as a trained convergence model, one or more local features associated with one or more corresponding landmarks, and to generate a determination of convergence for the landmark based on the local features and the trained convergence model. As one example, the convergence validator 546 can generate a quantitative score relative to an ideal convergence state for each landmark based on its local features. As one example, an ideal convergence state can be represented by any quantitative value, including 0, 1, −1, infinity, negative infinity, or the like. As another example, a quantitative value can be any real, complex, imaginary, scalar, vector or like value, or combination thereof. In some implementations, convergence validator 546 is operable by the parallel processor to execute parallel validation of a plurality of landmarks.

The recursion controller 548 is operable to control, begin, modify, block, and the like a recursion process governing the refinement engine 540 or any component thereof. In some implementations, the recursion controller 548 is operable to cause the refinement engine to continue iteration through one or more of the resolution controller 542, the landmark positioner 544, and the convergence validator 546 until a convergence condition is reached. In some implementations, a convergence condition is or includes a local maximum, local minimum, absolute maximum, or absolute minimum associated with an ideal convergence state. As one example, the recursion controller can block further recursion associated with a particular landmark when a quantitative score associated with that landmark reaches an ideal convergence state associated with that landmark. As another example, the recursion controller 548 can block further recursion associated with a particular landmark after a predetermined number of iterations of the refinement engine 540 with respect to a particular landmark or a predetermined number of total iterations of the refinement engine 540.

The warping metric database 550 includes one or more warping metrics indicating whether a landmark is placed at an optimal location with respect to a warp of a target model. In some implementations, the warping metrics includes one or more vectors indicating a correspondence between an expected orientation, distance, or the like, of a landmark at the reference model and an actual orientation, distance, or the like, of the landmark at the target model. In some implementations, the warping metric database 550 includes one or more warping metrics corresponding specifically to particular warps between particular landmarks having predetermined landmark identifiers, coordinates, or the like. As one example, the warping metric database 550 can include a first set of one or more warping metrics operable to quantify correspondence of a landmark to a particular warp at a particular local area of a target model. As another example, the warping metric database 550 can include a second set of one or more warping metrics operable to quantify correspondence of a landmark to another particular warp at a another particular local area of a target model.

In some implementations, the warping metric database 550 is or includes one or more vector-based transformation operations based on a particular bit-length of the vector corresponding to a distance within a particular coordinate space. In some implementations, the bit length corresponds to a particular range at a predetermined resolution within the coordinate space. As one example, a bit length can correspond to a first distance at a first resolution, or a second distance half as long as the first distance at a second resolution twice as high as the first resolution. It is to be understood that the bit length, range, and resolution can include any linear or nonlinear relationship. It is to be further understood that transformation data structures other than or in addition to vectors can comprise the convergence metric database 530.

The warping engine 560 is operable to modify one or more landmark positions in accordance with one or more warping metrics. In some implementations, the warping engine 560 is operable to execute one or more transformation processes by the transform processor 430. In some implementations, the warping engine 560 is operable to execute one or more parallel processes by the parallel processor 430. In some implementations, the warping engine 560 iterates placement of landmarks until determining that the particular landmark has a reached convergence position according to one or more warping metrics. In some implementations, the warping engine 560 includes a warp generator 562 and a recursion control channel 504.

The warp generator 562 is operable to generate one or more geometric shapes through one or more landmarks of a target model. In some implementations, the warp generator 562 is operable to obtain one or more warps from a reference model and generate corresponding warps at a target model. In some implementations, the warp generator generates a particular warp through landmarks of target model corresponding to a warp through corresponding landmarks of a reference model. The warp generator 562 is operable to modify, distort, or the like at least one landmark coordinate associated with a target model in accordance with one or more warping metrics. In some implementations, the warp generator 562 is or include a machine learning engine operable to obtain one or more warping metrics from the warping metric database 550 as a trained convergence model, one or more local features associated with one or more corresponding warps, and to generate a determination of convergence for the warps based on the local features and the trained convergence model. As one example, the warp generator 562 can generate a quantitative score relative to an ideal convergence state for each landmark based on its local features across the entire warp or any portion or subset thereof. In some implementations, warp generator 562 is operable by the parallel processor to execute parallel validation of a plurality of warps.

The recursion control channel 504 is operable to transmit recursion control instructions and determinations between the warping engine 560 and the recursion controller 548. In some implementations, the recursion controller 548 controls when to block iteration of the warping engine 560 for iterative warping of one or more warps. In some implementations, the recursion control channel 504 includes one or more logical, digital, analog, or like communication channels, lines, traces, or the like. In some implementations, the recursion control channel 504 includes a logical address to a header, interface, application programming interface, PUT interface, POST interface, or the like, associated with the refinement engine 540.

The warp communication channel 506 is operable to apply one or more transformations, translations, or the like to one or more landmarks of a landmark model of the landmark model database 510. The warp communication channel 506 is operable to communicatively couple the warping engine 560 to the landmark model database 510. In some implementations, the warp communication channel 506 is operable to communicate one or more instructions, signals, conditions, states, or the like between one or more of the warping engine 560 and the landmark model database 510. In some implementations, the warp communication channel 506 includes one or more logical, digital, analog, or like communication channels, lines, traces, or the like. In some implementations, the warp communication channel 506 includes a logical address to a header, interface, application programming interface, PUT interface, POST interface, or the like, associated with the warping engine 560.

Figure 6:
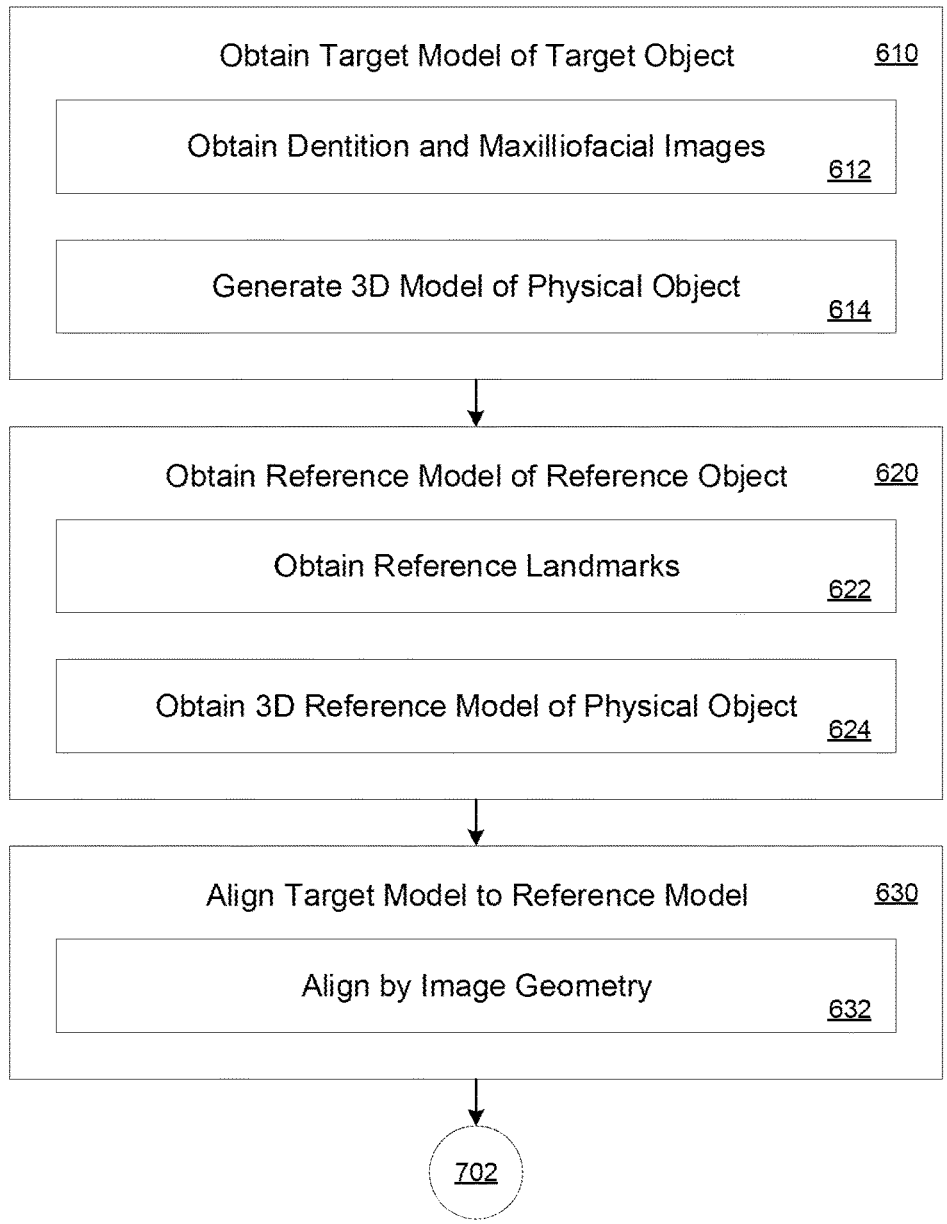
FIG. 6 illustrates an example method of aligning reference landmarks to a target object model, in accordance with present implementations.

FIG. 6 illustrates an example method of aligning reference landmarks to a target object model, in accordance with present implementations. In some implementations, at least one of the example processing system 400 and the example computing system 500 performs method 600 according to present implementations. In some implementations, the method 600 begins at step 610.

At step 610, the example system obtains a target model associated with a target object. In some implementations, step 610 includes at least one of steps 612 and 614. At step 612, the example system obtains at least one of a dentition image and a maxillofacial image. At step 614, the example system generates at least one three-dimensional model of a physical object. The method 600 then continues to step 620.

At step 620, the example system obtains at least one reference model associated with at least one corresponding reference object. In some implementations, step 620 includes at least one of steps 622 and 624. At step 622, the example system obtains one or more reference landmarks.

In some implementations, the obtained reference landmarks include secondary reference landmarks. At step 624, the example system obtains at least one three-dimensional model associated with at least one corresponding reference model of a physical object. The method 600 then continues to step 630.

At step 630, the example system aligns the target model to the reference model. In some implementations, step 630 includes step 632. At step 632, the example system aligns the target model and the reference model by image geometry. In some implementations, image geometry includes one or more planes or axes common to the reference model and the target model. In some implementations, the method 600 then continues to step 702.

Figure 7:
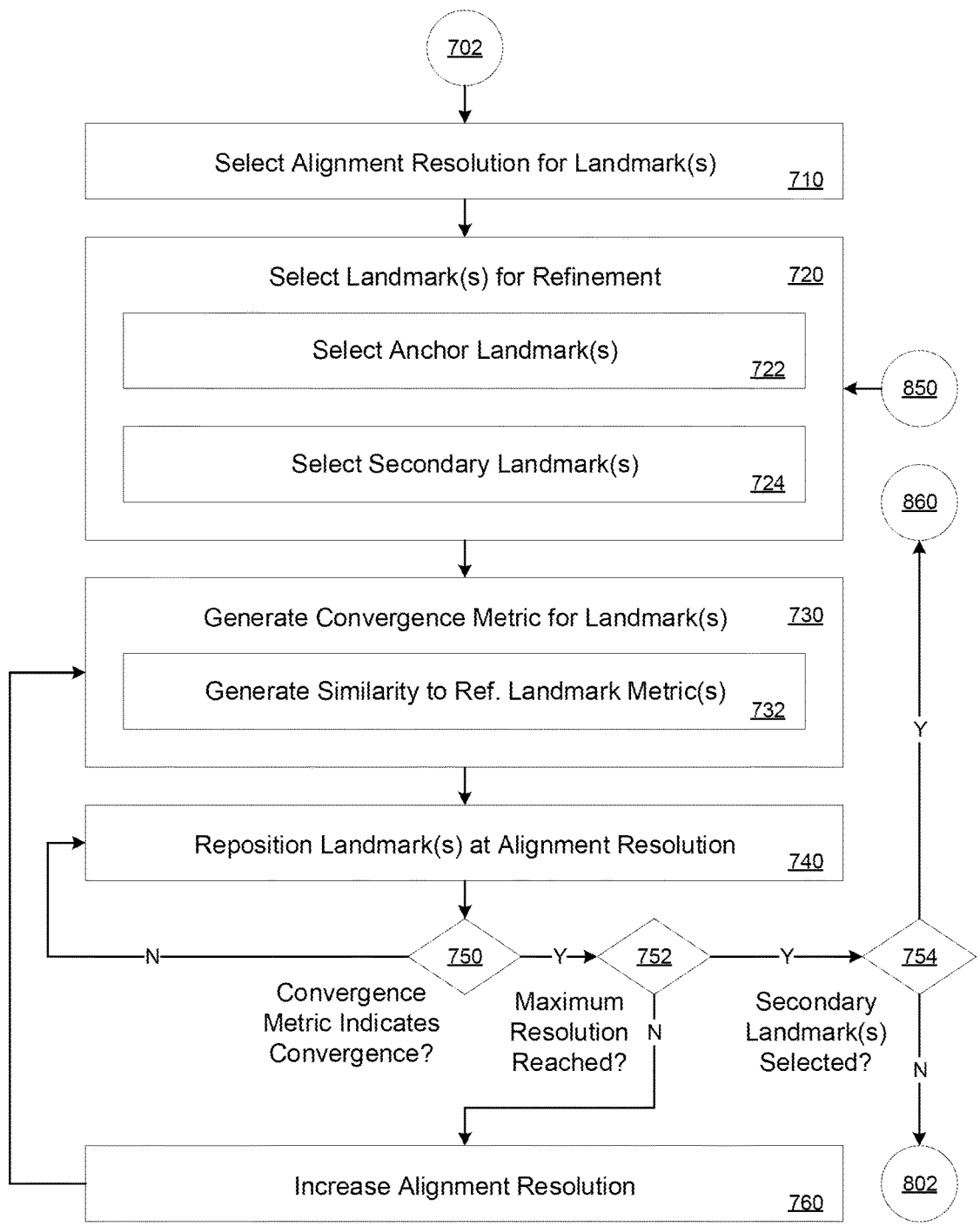
FIG. 7 illustrates an example method of aligning reference landmarks to a target object model further to the example method of FIG. 6.

FIG. 7 illustrates an example method of aligning reference landmarks to a target object model further to the example method of FIG. 6. In some implementations, at least one of the example processing system 400 and the example computing system 500 performs method 700 according to present implementations. In some implementations, the method 700 begins at step 702. The method 700 then continues to step 710.

At step 710, the example system selects an alignment resolution associated with the landmarks. In some implementations, the alignment resolution includes a minimum distance between points of a coordinate system associated with the target model. As one example, the minimum distance can be a percentage of an overall dimension of the target model in one axis. As another example, the minimum distance can be a number of pixels or an absolute distance less than a total distance across the target model in a particular axis or direction. The method 700 then continues to step 720.

At step 720, the example system selects one or more landmarks for refinement. In some implementations, step 720 includes at least one of steps 722 and 724. At step 722, the example system selects one or more anchor landmarks. As one example, anchor landmarks can correspond to landmarks obtained and refined in FIGS. 1A-2B. At step 724, the example system selects one or more secondary landmarks.

As one example, secondary landmarks can correspond to landmarks obtained and located in FIG. 3B. The method 700 then continues to step 730.

At step 730, the example system generates at least one convergence metric associated with at least one corresponding landmark. In some implementations, step 730 includes step 732. At step 732, the example system generates at least one similarity metric with respect to at least one landmark. In some implementations, a similarity metric corresponding to a determine whether a region surrounding a particular target landmark in a target model corresponds to a particular percentage or the like with a corresponding region surrounding a particular correspond reference landmark in a reference model. As one example, the similarity metric can determine the extent to which a features surrounding a target landmark matches a features surrounding its corresponding reference landmarks by one or more metric-based processes. The method 700 then continues to step 740. At step 740, the example system repositions at least one landmark at the alignment resolution. The method 700 then continues to step 750.

At step 750, the example system determines whether the convergence metric indicates convergence at the alignment resolution. In accordance with a determination that the convergence metric indicates convergence at the alignment resolution, the method 700 continues to step 752. In some implementations, the convergence metric can include or be associated with a check to constrain this part of the process to a maximum number of iterations. As one example, if the convergence metric does not indicate convergence and the maximum number of iterations has been exceeded, then the method 700 can continue to step 740 using the position at which the landmark had the best score based on the requirements set by the convergence metric. Alternatively, in accordance with a determination that the convergence metric does not indicate convergence at the alignment resolution, the method 700 continues to step 740.

At step 752, the example system determines whether a maximum alignment resolution is reached. In some implementations, maximum alignment resolution is a predetermined minimum distance between coordinates in a coordinate space. As one example, a maximum alignment resolution can be defined by a distance, pixel distance, percentage of a dimension of a target model in a particular direction, or the like. In accordance with a determination that a maximum alignment resolution is reached, the method 700 continues to step 754. Alternatively, in accordance with a determination that a maximum alignment resolution is not reached, the method 700 continues to step 760.

At step 754, the example system determines whether a secondary landmark is selected. In accordance with a determination that a secondary landmark is selected, the method 700 continues to step 860. Alternatively, in accordance with a determination that a secondary landmark is not selected, the method 700 continues to step 802.

At step 760, the example system increases an alignment resolution. As one example, the example system can increase the alignment resolution by reducing a minimum distance of a coordinate space by a percentage or absolute amount. The method 700 then continues to step 730.

Figure 8:
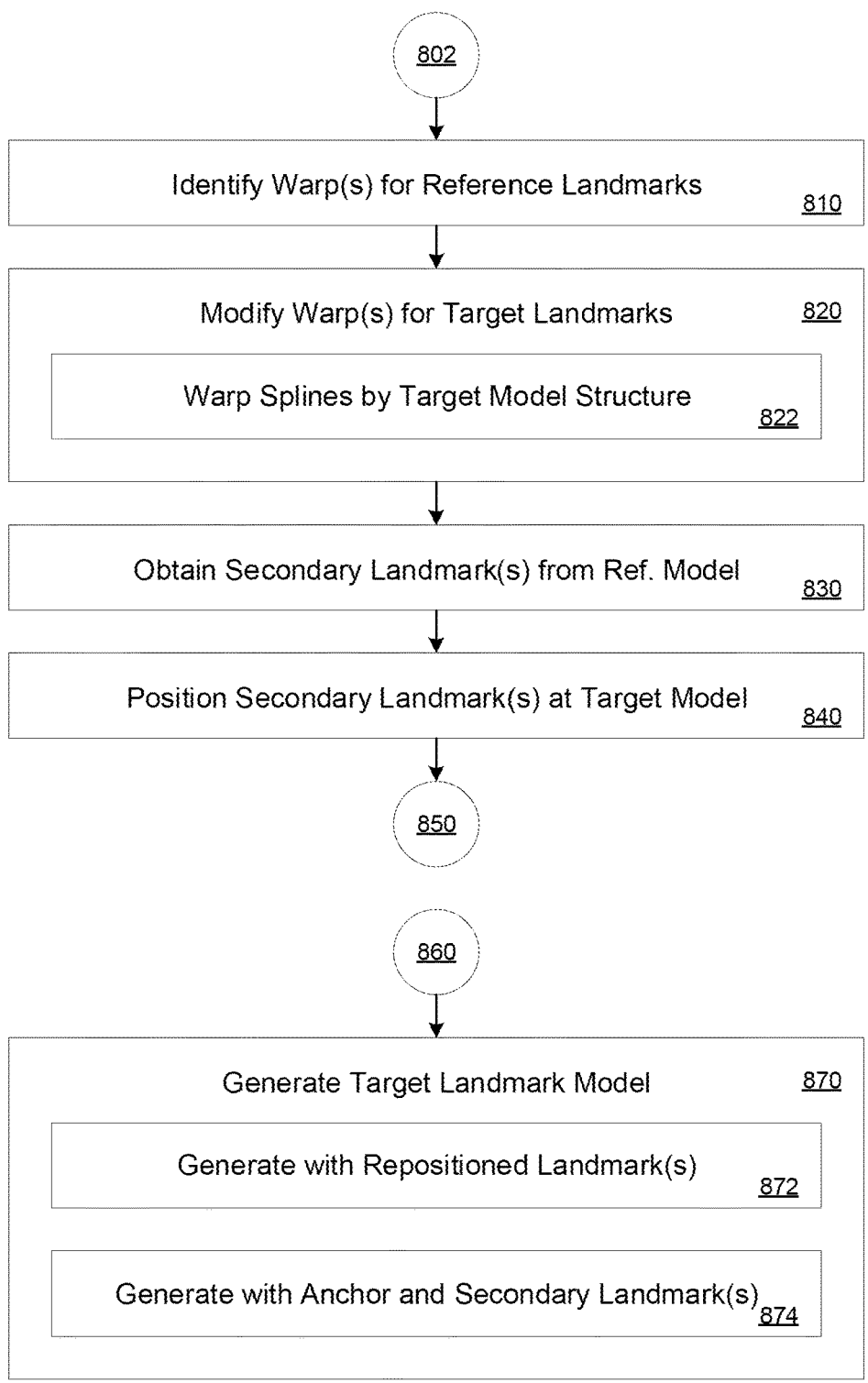
FIG. 8 illustrates an example method of aligning reference landmarks to a target object model further to the example method of FIG. 7.

FIG. 8 illustrates an example method of aligning reference landmarks to a target object model further to the example method of FIG. 7. In some implementations, at least one of the example processing system 400 and the example computing system 500 performs method 800 according to present implementations. In some implementations, the method 800 begins at step 802. The method 800 then continues to step 810.

At step 810, the example system generates at least one warp associated with one or more reference landmarks. As one example, the example system can identify at least one warp by obtaining a reference warp with reference landmarks corresponding to particular target landmarks, and generating a target warp terminating at the particular target landmarks and having a shape corresponding to the reference landmarks. The method 800 then continues to step 820.

At step 820, the example system modifies at least one warp associated with one or more target landmarks. In some implementations, step 820 includes step 822. At step 822, the example system modifies the warp in accordance with a structure of the target model. The method 800 then continues to step 830.

At step 830, the example system obtains at least one secondary landmark from the reference model. The method 800 then continues to step 840. At step 840, the example system positions the secondary landmark at the target model. The method 800 then continues to step 850. At step 860, the example system continues from 754. The method 800 then continues to step 870. At step 870, the example system generates at least one target landmark model. In some implementations, step 870 includes at least one of steps 872 and 874. At step 872, the example system generates the target landmark model with at least one repositioned landmark. In some implementations, the landmarks is repositioned relative to its distance to one or more target warps. At step 874, the example system generates the target model with at least one anchor landmark and at least one secondary landmark. In some implementations, the method 800 ends at step 870.

The herein described subject matter sometimes illustrates different components contained within, or connected with, different other components. It is to be understood that such depicted architectures are illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Further, unless otherwise noted, the use of the words "approximate," "about," "around," "substantially," etc., mean plus or minus ten percent.

The foregoing description of illustrative implementations has been presented for purposes of illustration and of description. It is not intended to be exhaustive or limiting with respect to the precise form disclosed, and modifications and variations are possible in light of the above teachings or may be acquired from practice of the disclosed implementations. It is intended that the scope of the invention be defined by the claims appended hereto and their equivalents.

What is claimed is:

1. A method of locating landmarks at a target object model, comprising:
   obtaining a target model associated with a target physical object, and a reference model associated with a reference physical object and including an anchor landmark coordinate;
   generating a convergence metric based on a structural property of the target model at the anchor landmark coordinate, a structural property of the reference model at the landmark coordinate, and an alignment resolution associated with a first quantized distance; and
   in accordance with a determination that the convergence metric satisfies a convergence heuristic and does not satisfy a resolution heuristic, associating the alignment resolution with a second quantized distance less than the first quantized distance, and modifying a position of the anchor landmark coordinate based on the alignment resolution.

2. The method of claim 1, further comprising:
   aligning the target model with the reference model in accordance with at least one geometric feature corresponding to the target model and the reference model.

3. The method of claim 1, further comprising:
   in accordance with a determination that the convergence metric does not satisfy the convergence heuristic, repeating the modifying the position of the anchor landmark coordinate.

4. The method of claim 1, further comprising:
   in accordance with a determination that the convergence metric satisfies the convergence heuristic and satisfies the resolution heuristic, associating a secondary landmark coordinate with the target model,
   wherein the reference model further includes the secondary landmark coordinate.

5. The method of claim 4, wherein the associating the secondary landmark coordinate with the target model comprises:
   generating a warp associated with the anchor landmark coordinate of the reference model and the anchor landmark coordinate of the target model.

6. The method of claim 5, wherein the generating the warp comprises generating the warp by transforming a first coordinate associated with a first coordinate space of the anchor landmark coordinate of the reference model to a second coordinate associated with a second coordinate space of the anchor landmark coordinate of the target model.

7. The method of claim 6, wherein the associating the secondary landmark coordinate with the target model further comprises:
   modifying the secondary landmark coordinate based on a topographical property of the reference model and a topographical property of the target model.

8. The method of claim 7, wherein the associating the secondary landmark coordinate with the target model further comprises:
   generating a secondary convergence heuristic based on a position of the secondary landmark coordinate.

9. The method of claim 8, wherein the associating the secondary landmark coordinate with the target model further comprises:
   generating a secondary convergence metric based on a position of the secondary landmark coordinate.

10. The method of claim 9, wherein the associating the secondary landmark coordinate with the target model further comprises:
    modifying a position of the secondary landmark coordinate, in accordance with the secondary convergence metric and the secondary convergence heuristic.

11. The method of claim 1, wherein the target physical object and the reference physical object each include at least one of a dentition structure and a maxillofacial structure.

12. A system of locating landmarks at a target object model, comprising:
    a coarse alignment engine operable to obtain a target model associated with a target physical object, and a reference model associated with a reference physical object and including an anchor landmark coordinate; and
    a refinement engine operatively coupled to the coarse alignment engine and operable to generate a convergence metric based on a structural property of the target model at the anchor landmark coordinate, a structural property of the reference model at the landmark coordinate, and an alignment resolution associated with a first quantized distance, and, in accordance with a determination that the convergence metric satisfies a convergence heuristic and does not satisfy a resolution heuristic, associate the alignment resolution with a second quantized distance less than the first quantized distance, and modify a position of the anchor landmark coordinate based on the alignment resolution.

13. The method of claim 12, wherein the refinement engine is further operable to, in accordance with a determination that the convergence metric satisfies the convergence heuristic and satisfies the resolution heuristic, associate a secondary landmark coordinate with the target model, and
    wherein the reference model further includes the secondary landmark coordinate.

14. The method of claim 13, further comprising:
    a warping engine operatively coupled to the refinement engine and operable to generate a reference warp associated with the anchor landmark coordinate of the reference model.

15. The method of claim 14, wherein the warping engine is further operable to generate a target warp associated with the anchor landmark coordinate of the target model.

16. The method of claim 15, wherein the warping engine is further operable to warp the target warp based on a topographical property of the reference model and a topographical property of the target model.

17. The method of claim 16, wherein the refinement engine is further operable to generate a secondary convergence heuristic based on a position of the secondary landmark coordinate relative to the reference warp.

18. The method of claim 17, wherein the refinement engine is further operable to generate a secondary convergence metric based on a position of the secondary landmark coordinate relative to the target warp.

19. The method of claim 18, wherein the refinement engine is further operable to modify a position of the secondary landmark coordinate relative to the reference warp and the warped target warp, in accordance with the secondary convergence metric and the secondary convergence heuristic.

20. A method of locating landmarks at a target object model, comprising:
- obtaining a target model associated with a target physical object, and a reference model associated with a reference physical object, the reference physical object including an anchor landmark coordinate and a secondary landmark coordinate;
- generating a reference warp associated with the anchor landmark coordinate of the reference model;
- generating a target warp associated with the anchor landmark coordinate of the target model;
- warping the target warp based on a topographical property of the target model;
- generating a secondary convergence heuristic based on a position of the secondary landmark coordinate relative to the reference warp;
- generating a secondary convergence metric based on a position of the secondary landmark coordinate relative to the target warp; and
- modifying a position of the secondary landmark coordinate relative to the reference warp and the warped target warp, in accordance with the secondary convergence metric and the secondary convergence heuristic.

* * * * *